(12) United States Patent
Mazurek et al.

(10) Patent No.: US 10,279,069 B2
(45) Date of Patent: May 7, 2019

(54) SHAPE MEMORY POLYMER ARTICLES WITH A MICROSTRUCTURED SURFACE

(75) Inventors: Mieczyslaw H. Mazurek, Roseville, MN (US); Robert K. Galkiewicz, Roseville, MN (US); Audrey A. Sherman, St. Paul, MN (US); James R. Starkey, Menomonia, WI (US); Wendi J. Winkler, Minneapolis, MN (US); Haiyan Zhang, Woodbury, MN (US); Jeffrey M. Olofson, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 756 days.

(21) Appl. No.: 13/296,362

(22) Filed: Nov. 15, 2011

(65) Prior Publication Data

US 2012/0058305 A1 Mar. 8, 2012

Related U.S. Application Data

(63) Continuation of application No. 11/460,685, filed on Jul. 18, 2006, now abandoned.

(51) Int. Cl.
| | |
|---|---|
| *C08G 77/00* | (2006.01) |
| *A61L 15/26* | (2006.01) |
| *A61L 15/24* | (2006.01) |
| *A61L 24/04* | (2006.01) |
| *A61L 24/06* | (2006.01) |

(Continued)

(52) U.S. Cl.
CPC .............. *A61L 15/26* (2013.01); *A61L 15/24* (2013.01); *A61L 24/046* (2013.01); *A61L 24/06* (2013.01); *C08F 283/00* (2013.01); *C08F 283/12* (2013.01); *C08F 290/068* (2013.01); *C08F 290/148* (2013.01); *A61L 2400/16* (2013.01); *Y10T 428/24355* (2015.01)

(58) Field of Classification Search
None
See application file for complete search history.

(56) References Cited

U.S. PATENT DOCUMENTS

| | | | |
|---|---|---|---|
| 1,905,716 A | 4/1933 | Ives | |
| 1,918,705 A | 7/1933 | Ives | |

(Continued)

FOREIGN PATENT DOCUMENTS

| | | |
|---|---|---|
| DE | 198 04 997 | 2/1999 |
| EP | 0175504 | 3/1986 |

(Continued)

OTHER PUBLICATIONS

Teegarden (Polymer Chemistry: Introduction to an Indispensable Science, NSTA press, 2004, p. 207).*

(Continued)

*Primary Examiner* — Rachel Kahn
(74) *Attorney, Agent, or Firm* — Jeffrey M. Olofson

(57) ABSTRACT

A shape memory polymer article is disclosed. The article may include a surface having a microstructure and it may include a shape memory polymer. The shape memory polymer may include a copolymer network. The copolymer network may be formed from the reaction product of a free radically polymerizable siloxane having greater than one functional free radically polymerizable group and at least one (meth)acrylate monomer.

22 Claims, 1 Drawing Sheet

(51) Int. Cl.
   *C08F 283/00* (2006.01)
   *C08F 283/12* (2006.01)
   *C08F 290/06* (2006.01)
   *C08F 290/14* (2006.01)

(56) References Cited

U.S. PATENT DOCUMENTS

| | | |
|---|---|---|
| 2,039,648 A | 5/1936 | Ives |
| 2,063,985 A | 12/1936 | Coffey |
| 2,279,825 A | 4/1942 | Kaszab |
| 2,326,634 A | 8/1943 | Gebhard |
| 2,500,511 A | 3/1950 | Bonnet |
| 2,622,472 A | 12/1952 | Bonnet |
| 2,833,176 A | 5/1958 | Ossoinak |
| 3,154,872 A | 11/1964 | Nordgren |
| 3,161,509 A | 12/1964 | Howe |
| 3,306,974 A | 2/1967 | Cunnally |
| 3,357,770 A | 12/1967 | Clay |
| 3,365,350 A | 1/1968 | Cahn |
| 3,442,569 A | 5/1969 | Bonnet |
| 3,459,111 A | 8/1969 | Cooper, Jr. |
| 3,503,315 A | 3/1970 | Montebello |
| 3,584,369 A | 6/1971 | Montebello |
| 3,607,273 A | 9/1971 | Kinney |
| 3,613,539 A | 10/1971 | Dudley |
| 3,676,130 A | 7/1972 | Burckhardt |
| 3,706,486 A | 12/1972 | de Montebello |
| 3,751,258 A | 8/1973 | Howe |
| 3,801,183 A | 4/1974 | Sevelin |
| 3,890,269 A | 6/1975 | Martin |
| 4,034,555 A | 7/1977 | Rosenthal |
| 4,082,426 A | 4/1978 | Brown |
| 4,099,838 A | 7/1978 | Cook |
| 4,121,011 A | 10/1978 | Glover |
| 4,200,875 A | 4/1980 | Galanos |
| 4,315,665 A | 2/1982 | Haines |
| 4,420,527 A | 12/1983 | Haines |
| 4,424,990 A | 1/1984 | White |
| 4,541,727 A | 9/1985 | Rosenthal |
| 4,541,830 A | 9/1985 | Hotta |
| 4,552,442 A | 11/1985 | Street |
| 4,557,590 A | 12/1985 | Winnek |
| 4,618,552 A | 10/1986 | Tanaka |
| 4,629,667 A | 12/1986 | Kistner |
| 4,632,895 A | 12/1986 | Patel |
| 4,634,220 A | 1/1987 | Hockert |
| 4,661,577 A | 4/1987 | Jo Lane |
| 4,668,063 A | 5/1987 | Street |
| 4,688,894 A | 8/1987 | Hockert |
| 4,691,993 A | 9/1987 | Porter |
| 4,700,207 A | 10/1987 | Vanier |
| 4,708,920 A | 11/1987 | Orensteen |
| 4,714,656 A | 12/1987 | Bradshaw |
| 4,732,453 A | 3/1988 | de Montebello |
| 4,743,526 A | 5/1988 | Ando |
| 4,757,350 A | 7/1988 | Street |
| 4,772,582 A | 9/1988 | DeBoer |
| 4,775,219 A | 10/1988 | Appeldorn |
| 4,783,141 A | 11/1988 | Baba |
| 4,799,739 A | 1/1989 | Newswanger |
| 4,833,124 A | 5/1989 | Lum |
| 4,876,235 A | 10/1989 | DeBoer |
| 4,927,238 A | 5/1990 | Green |
| 4,935,335 A | 6/1990 | Fotland |
| 5,026,890 A | 6/1991 | Webb |
| 5,064,272 A | 11/1991 | Bailey |
| 5,091,483 A | 2/1992 | Mazurek |
| 5,105,206 A | 4/1992 | Sarraf |
| 5,122,902 A | 6/1992 | Benson |
| 5,169,707 A | 12/1992 | Faykish |
| 5,214,119 A | 5/1993 | Leir |
| 5,244,288 A | 9/1993 | Nagaoka |
| 5,254,390 A | 10/1993 | Lu |
| 5,264,278 A | 11/1993 | Mazurek |
| 5,276,122 A | 1/1994 | Aoki |
| 5,279,912 A | 1/1994 | Telfer |
| 5,308,737 A | 5/1994 | Bills |
| 5,326,619 A | 7/1994 | Dower |
| 5,330,799 A | 7/1994 | Sandor |
| 5,359,454 A | 10/1994 | Steenblik |
| 5,360,694 A | 11/1994 | Thien |
| 5,364,740 A | 11/1994 | Fohrenkamm |
| 5,449,597 A | 9/1995 | Sawyer |
| 5,455,689 A | 10/1995 | Taylor |
| 5,459,016 A | 10/1995 | Debe |
| 5,461,134 A | 10/1995 | Leir |
| 5,491,045 A | 2/1996 | DeBoer |
| 5,493,427 A | 2/1996 | Nomura |
| 5,506,300 A | 4/1996 | Ward |
| 5,512,650 A | 4/1996 | Leir |
| 5,514,730 A | 5/1996 | Mazurek |
| 5,521,035 A | 5/1996 | Wolk |
| 5,554,432 A | 9/1996 | Sandor |
| 5,589,246 A | 12/1996 | Calhoun |
| 5,594,841 A | 1/1997 | Schutz |
| 5,639,580 A | 6/1997 | Morton |
| 5,642,226 A | 6/1997 | Rosenthal |
| 5,644,431 A | 7/1997 | Magee |
| 5,671,089 A | 9/1997 | Allio |
| 5,680,171 A | 10/1997 | Lo |
| 5,681,676 A | 10/1997 | Telfer |
| 5,685,939 A | 11/1997 | Wolk |
| 5,689,372 A | 11/1997 | Morton |
| 5,706,132 A | 1/1998 | Nestegard |
| 5,712,731 A | 1/1998 | Drinkwater |
| 5,717,844 A | 2/1998 | Lo |
| 5,744,291 A | 4/1998 | Ip |
| 5,757,550 A | 5/1998 | Gulick, Jr. |
| 5,843,617 A | 12/1998 | Patel |
| 5,850,278 A | 12/1998 | Lo |
| 5,850,580 A | 12/1998 | Taguchi |
| 5,856,061 A | 1/1999 | Patel |
| 5,889,118 A | 3/1999 | Delgado |
| 5,894,069 A | 4/1999 | Wen |
| 5,896,230 A | 4/1999 | Goggins |
| 5,935,758 A | 8/1999 | Patel |
| 5,945,249 A | 8/1999 | Patel |
| 5,994,026 A | 11/1999 | DeBoer |
| 6,057,067 A | 5/2000 | Isberg |
| 6,084,713 A | 7/2000 | Rosenthal |
| 6,092,465 A | 7/2000 | Agronin |
| 6,110,645 A | 8/2000 | DeBoer |
| 6,197,474 B1 | 3/2001 | Niemeyer |
| 6,228,555 B1 | 5/2001 | Hoffend, Jr. |
| 6,242,152 B1 | 6/2001 | Staral |
| 6,285,001 B1 | 9/2001 | Fleming |
| 6,288,842 B1 | 9/2001 | Florczak |
| 6,291,143 B1 | 9/2001 | Patel |
| 6,355,759 B1 | 3/2002 | Sherman |
| 6,369,844 B1 | 4/2002 | Neumann |
| 6,388,043 B1 | 5/2002 | Langer |
| 6,468,715 B2 | 10/2002 | Hoffend, Jr. |
| 6,569,521 B1 | 5/2003 | Sheridan |
| 6,827,325 B2 | 12/2004 | Hofmann |
| 6,986,855 B1 | 1/2006 | Hood |
| 7,068,434 B2 | 6/2006 | Florczak |
| 7,106,519 B2 | 9/2006 | Aizenberg |
| 7,245,430 B2 | 7/2007 | Kobayashi |
| 7,253,958 B2 | 8/2007 | Aizenberg |
| 7,336,422 B2 | 2/2008 | Dunn |
| 7,586,685 B2 | 9/2009 | Dunn |
| 7,951,319 B2 | 5/2011 | Sherman |
| 7,981,499 B2 | 7/2011 | Endle |
| 2002/0145807 A1 | 10/2002 | Nishikawa |
| 2005/0275946 A1 | 12/2005 | Choo |
| 2006/0051540 A1 | 3/2006 | Kagawa |
| 2006/0262411 A1 | 11/2006 | Dunn |
| 2007/0081254 A1 | 4/2007 | Endle |
| 2008/0024872 A1 | 1/2008 | Dunn |

(56) References Cited

U.S. PATENT DOCUMENTS

| | | |
|---|---|---|
| 2008/0027199 A1 | 1/2008 | Mazurek |
| 2011/0198781 A1 | 8/2011 | Sherman |

FOREIGN PATENT DOCUMENTS

| | | |
|---|---|---|
| EP | 0363919 | 4/1990 |
| EP | 0404004 | 12/1990 |
| EP | 0583766 | 2/1994 |
| EP | 0615860 | 9/1994 |
| EP | 0655347 | 5/1995 |
| EP | 0658443 | 6/1995 |
| EP | 0673785 | 9/1995 |
| EP | 0688351 | 12/1995 |
| EP | 1079274 | 2/2001 |
| GB | 1308116 | 2/1973 |
| GB | 1433025 | 4/1976 |
| GB | 2083726 | 3/1982 |
| JP | 01065153 | 3/1989 |
| JP | 02105101 | 8/1990 |
| JP | 03068610 | 3/1991 |
| JP | 03068611 | 3/1991 |
| JP | 4309583 | 11/1992 |
| JP | 7281327 | 10/1995 |
| JP | 09076245 | 3/1997 |
| JP | 2001-219472 | 8/2001 |
| KR | 1990-0006110 | 5/1990 |
| WO | 1983-03019 | 9/1983 |
| WO | 1995-26281 | 10/1995 |
| WO | 1997-15173 | 4/1997 |
| WO | 1997-46631 | 12/1997 |
| WO | 1998-14803 | 4/1998 |
| WO | 1999-37949 | 7/1999 |
| WO | 1999-42147 | 8/1999 |
| WO | 2003-061983 | 7/2003 |
| WO | 2003-093341 | 11/2003 |
| WO | 2008-014142 | 1/2008 |
| WO | 2008-014167 | 1/2008 |

OTHER PUBLICATIONS

3MTM Authentication Reader Product Fact Sheet, 3M Security Systems Division, 2004, 4 pages.
3MTM ePassport Reader Product Fact Sheet, 3M Security Systems Division, 2004, 6 pages.
3MTM Full Page Reader Product Fact Sheet, 3M Security Systems Division, 2004, 6 pages.
3MTM Inspection Reader Product Fact Sheet, 3M Security Systems Division, 2004, 2 pages.
Dudnikov, "Obtaining a portrait of a person by the integral photography method," Opt. Mekh. Promst. Dec. 1979, vol. 47, pp. 55-56.
Dudnikov, "Raster Systems for Obtaining Dimensional Images," Raster 3D Imaging Systems, 1986, pp. 102-173, 190-199, 206-209.
Dudnikov, "Selecting the parameters of the lens-array photographing system in integral photography," Opt. Mekh. Promst. Feb. 1977, vol. 45, pp. 13-15.
Factiva, "Shape-memory polymers offer new twist on applications", Modern Plastics International, Chemical Business NewsBase, Apr. 24, 2003, 1 page.
Gall, "Thermomechanics of the shape memory effect in polymers for biomedical applications," Journal of Biomedical Materials Research Part A, Apr. 2005, vol. 73A, No. 3, pp. 339-348.
Kim, "Polyurethanes having shape memory effects", Polymer, vol. 37 No. 26, pp. 5781-5793, 1996.
Lendlein, "AB-polymer networks based on oligo($\epsilon$-caprolactone) segments showing shape-memory properties", PNAS, vol. 98 No. 3, 2001, pp. 842-847.
Lendlein, "Biodegradable, Elastic Shape-Memory Polymers for Potential Biomedical Applications", Science, May 31, 2002, vol. 296, pp. 1673-1676.
Lendlein, "Shape-Memory Effect, From temporary shape . . . to permanent shape, Shape-Memory Polymers", Angewandte Chemie Int. Ed., 2002, vol. 41, pp. 2034-2057.
Lendlein, "Shape-memory polymers as stimuli-sensitive implant materials", Clinical Hemorheology and Microcirculation, 2005, vol. 32, No. 2, pp. 105-116. XP008049331.
Lippmann, "G. Lippmann's Integral Photography Method Limitations", 4 pages.
Mazurek, "Novel Materials Based on Silicone-Acrylate Copolymer Networks", Journal of Applied Polymer Science, 2001, vol. 80, pp. 159-180.
Okano, "Hydrophilic-hydrophobic microdomain surfaces having an ability to suppress platelet aggregation and their in vitro antithrombogenicity," Journal of Biomedical Materials Research, 1986, vol. 20, No. 7, pp. 919-927.
Processing and Display of Three-Dimensional Data II, SPIE vol. 507, 1 page, 1984.
Smith, Modern Optical Engineering, The Design of Optical Systems, 5.3 Characteristics of the Eye, Visual Acuity, 1966, pp. 104-105.
Weekly Reports of the Meetings of the Academy of Science, Photograph—Reversible print. Complete photographs. Note of Mr. G. Lippman, vol. 146, pp. 446-451, 1908.
Search Report for PCT/US2007/073097, 3 pages, dated Nov. 29, 2007.
Search Report for PCT/US2007/073825, 3 pages, dated Dec. 27, 2007.
Search Report for PCT/US2007/073649, 3 pages, dated Dec. 30, 2009.
Zhongqiang Yang, Thermal and UV Shape Shifting of Surface Topography, JACS Communications, Published on Web Jan. 10, 2006, 2006 American Chemical Society 2006, 128, pp. 1074-1075.

* cited by examiner

SHAPE MEMORY POLYMER ARTICLES WITH A MICROSTRUCTURED SURFACE

CROSS-REFERENCE TO RELATED APPLICATIONS

This application is a continuation of U.S. Ser. No. 11/460,685, filed Jul. 28, 2006, pending; which is related to U.S. patent application Ser. No. 11/460,682, filed Jul. 28, 2006 now issued as U.S. Pat. No. 7,951,319 on May 31, 2011; and also related to U.S. patent application Ser. No. 11/495,999, filed Jul. 28, 2006, now issued as U.S. Pat. No. 7,586,685 on Sep. 8, 2009.

FIELD OF THE INVENTION

The invention relates to shape memory polymers, and particularly, to shape memory polymers having microstructured surfaces.

BACKGROUND

Shape memory materials have the unique ability to "remember" a pre-set shape and, upon exposure to the appropriate stimuli, shift from a deformed or altered shape back to the pre-set shape. Several commercially important uses have been developed for shape memory materials. For example, shape memory metal alloys are commonly used in various medical, dental, mechanical, and other technology areas for a wide variety of products.

Shape memory polymers and the uses of these materials have emerged more recently. However, the basic premise behind these materials is the same—that the material can be pre-set in a particular shape, deformed, and then revert back to the pre-set shape when exposed to the appropriate stimuli.

SUMMARY

The present disclosure relates generally to shape memory polymer articles. The shape memory polymer articles may include a microstructured surface.

In one embodiment, an illustrative article is described that includes a polymeric member. The polymeric member may include a surface having a microstructure and it may include a shape memory polymer. The shape memory polymer may include a copolymer network. The copolymer network may include the reaction product of a free radically polymerizable siloxane having greater than one functional free radically polymerizable group and at least one (meth)acrylate monomer. The at least one (meth)acrylate monomer, when homopolymerized, may form a homopolymer that has a glass transition temperature, a melting temperature, or both greater than about 40° C.

In another embodiment, an illustrative article is described that includes a polymeric member having a microstructured surface. The microstructured surface may include a surface feature that is not visible to an unaided eye. The polymeric member may include a shape memory polymer.

In yet another embodiment, an illustrative article is described that includes a polymeric member having a microstructured surface. The microstructured surface may include a surface feature that is not visible to an unaided eye. The polymeric member may include a shape memory polymer. The shape memory polymer may include a copolymer network. The copolymer network may include the reaction product of (meth)acryloxyurea siloxane and isobornyl acrylate.

The above summary of the present invention is not intended to describe each disclosed embodiment or every implementation of the present invention. The Figures, Detailed Description and Examples, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
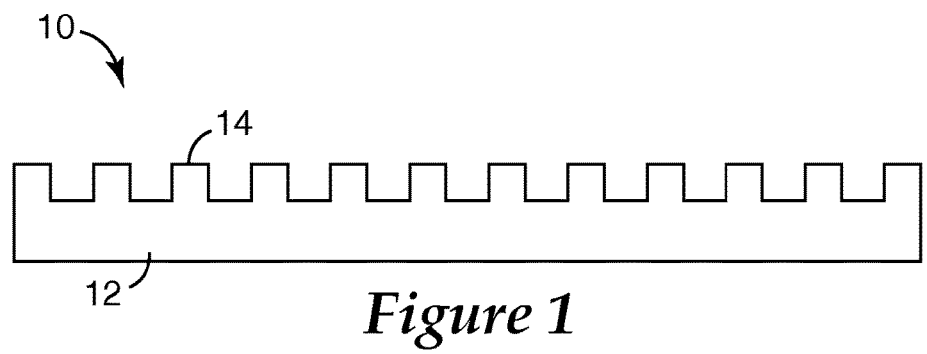
FIG. 1 is a side view of an illustrative article having a surface with a microstructure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Generally, this disclosure is directed to shape memory polymer articles that have a microstructured surface. While the present invention is not so limited, an appreciation of various aspects of the invention will be gained through discussion of the various features and components provided below.

Selected Definitions

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the term "alkyl" refers to a straight or branched chain monovalent hydrocarbon radical optionally containing one or more heteroatomic substitutions independently selected from S, O, Si, or N. Alkyl groups generally include those with one to twenty atoms. Alkyl groups may be unsubstituted or substituted with those substituents that do not interfere with the specified function of the composition. Substituents include alkoxy, hydroxy, mercapto, amino, alkyl substituted amino, or halo, for example. Examples of "alkyl" as used herein include, but are not limited to, methyl, ethyl, n-propyl, n-butyl, n-pentyl, isobutyl, and isopropyl, and the like.

As used herein, the term "aryl" refers to monovalent unsaturated aromatic carbocyclic radicals having a single ring, such as phenyl, or multiple condensed rings, such as naphthyl or anthryl. Aryl groups may be unsubstituted or substituted with those substituents that do not interfere with the specified function of the composition. Substituents include alkoxy, hydroxy, mercapto, amino, alkyl substituted amino, or halo, for example. Such an aryl ring may be optionally fused to one or more of another heterocyclic ring(s), heteroaryl ring(s), aryl ring(s), cycloalkenyl ring(s), or cycloalkyl rings. Examples of "aryl" as used herein include, but are not limited to, phenyl, 2-naphthyl, 1-naphthyl, biphenyl, 2-hydroxyphenyl, 2-aminophenyl, 2-methoxyphenyl and the like.

As used herein the term (meth)acrylate is used to define both acrylates and methacrylates.

The term telechelic siloxane refers to siloxanes with 2 reactive groups, one at either end of the siloxane chain.

As used herein, the term shape memory polymer refers to polymeric materials that are stimuli-responsive. Upon application of an external stimuli they have the ability to change their shape. A change in shape initiated by a change in temperature can be referred to as a thermally induced shape memory effect. While not being bound by theory, the shape memory effect may result from the polymer's structure, that is, its morphology in combination with a certain processing and programming technology. Therefore, the shape-memory behavior can be observed for several polymers that may differ significantly in their chemical composition.

Articles

The present disclosure is directed to articles. The articles may include a polymeric member that has a surface with a microstructure and that includes a shape memory polymer. The articles contemplated span a vast array of technical fields and include essentially any structure that may find utility or otherwise benefit from having a shape memory polymer incorporated into their construction. This may include a variety of different devices, apparatuses, components or portions of devices, layers or surfaces on devices, and the like, or any other suitable structure. For example, the articles of this disclosure may include an adhesive, a tape or substrate including an adhesive, a heat-activated tape, a microstructured tape, a backing member, a foam tape, a device having a fluid disposed or encapsulated therein, a microfluidic device, a circuit or circuit board, a printed circuit, a film (including multilayer optical films), a micromachined article, an embossed article, a printing plate or film used to create 3D prints, a substrate for pattern coating and/or pattern printing, an electrode, a device having cube corners with retroreflective characteristics, a secure identification article, a secure license or license plate, a directional organic light emitting diode, a sensor, an indicator, a switch, and the like, or any other suitable device. It should be noted that this list of articles is not intended to be limiting as the articles contemplated can take the form of any suitable structure, apparatus, or device.

As indicated above, an exemplary article may include a shape memory polymer. Some examples of shape memory polymers suitable for the articles are described in more detail below. In some embodiments, the entire article is made from the shape memory polymer. In other embodiments, only a portion of the article is made from a shape memory polymer. This may include a shape memory polymer layer, a shape memory polymer surface, a shape memory polymer portion, or any other suitable configuration. When only a portion of the article is made from a shape memory polymer, the remaining materials making up the article may include metals, metal alloys, polymers, ceramics, and the like, or any other suitable material. Regardless of whether the article is completely or partially made from a shape memory polymer, the articles described herein can be described as "shape memory polymer articles".

Shape memory polymers are known to have the unique ability to be set in a pre-set shape, deformed to an altered shape, and then revert back to the pre-set shape when exposed to the appropriate stimuli (e.g., changes in temperature, application of solvent, etc.). Because the articles disclosed herein include a shape memory polymer, the portion of the article (or all of the article if made completely from a shape memory polymer) having the shape memory polymer can be configured to utilize this property. For example, the article may include a shape memory polymer surface that has been cast or otherwise shaped to have a pre-set shape or configuration. This surface can be deformed to an altered or deformed shape and then be shifted back to the pre-set shape when appropriately cued. Triggering the shift from the deformed shape to the pre-set shape can vary depending on the particular polymer used or other parameters. However, at least some of the shape memory polymers disclosed herein can be shifted by exposure to elevated temperatures and/or to an appropriate solvent.

Also as indicated above, the articles include a surface having a microstructure. Generally, a surface with a microstructure is different than a "flat" or unstructured surface. As used herein, the term "microstructure" means the configuration of features wherein at least 2 dimensions of the features are microscopic. The topical and/or cross-sectional view of the features, therefore, are microscopic. As used herein, the term "microscopic" refers to features of small enough dimension so as to require an optic aid to the naked eye when viewed from any plane of view to determine its shape. One criterion is found in Modern Optic Engineering by W. J. Smith, McGraw-Hill, 1966, pages 104-105 whereby visual acuity, " . . . is defined and measured in terms of the angular size of the smallest character that can be recognized." Normal visual acuity is considered to be when the smallest recognizable letter subtends an angular height of 5 minutes of arc on the retina. At a typical working distance of 250 mm (10 inches), this yields a lateral dimension of 0.36 mm (0.0145 inch) for this object.

The microstructures may be formed along portions or all of any number of surfaces of the article. For example, some surfaces of the articles may include sections that have microstructures and sections that are free from microstructures. Alternatively, substantially all of one or more surfaces of the articles may include microstructures. In addition, the shape and/or configuration of the microstructures can also vary. For example, microstructures can include one or more projections, one or more depressions, a combination of projections and depressions, ridges, posts, pyramids, hemispheres, cones, protrusion, or any other suitable feature. The shapes of the various projections and/or depressions can also vary. For example, some embodiments of projections and/or depressions can be rounded in shape (e.g., circular, semicircular, spherical, hemispherical, oval, pill-shaped, partially pill-shaped, etc.) or include a rounded portion, polygonal in shape or include a polygonal portion (e.g., triangular, squared, cubed including cube corners, tetrahedrical, rectangular, paralleopiped, pentagonal, hexagonal, etc.), an irregular shape, a regular shape, a pointed shape, a truncated shape, combinations thereof, or any other suitable shape. In at least some of these as well as in other embodiments, the projections and/or depressions may include or define one or more channels, valleys, wells, ridges, and the like, combinations thereof, or any other configuration.

Microstructures may be formed in a surface of an article through the use of a microstructured molding tool. A microstructured molding tool is an implement for imparting a structure or finish to at least a portion of an article and that may be continuously reused in the process. Microstructured molding tools can be in the form of a planar stamping press, a flexible or inflexible belt, a roller, or the like. Furthermore, microstructured molding tools are generally considered to be tools from which the microstructured surface feature is generated by embossing, coating, casting, or platen pressing and do not become part of the finished microstructured article. Instead, a surface on the article corresponding to where the article came into contact with the microstructured surface of the molding tool defines the microstructure or microstructured surface feature of the article.

A broad range of methods are known to those skilled in this art for generating microstructured molding tools. Examples of these methods include but are not limited to photolithography, etching, discharge machining, ion milling, micromachining, and electroforming. Microstructured molding tools can also be prepared by replicating various microstructured surfaces, including irregular shapes and patterns, with a moldable material such as those selected from the group consisting of crosslinkable liquid silicone rubber, radiation curable urethanes, etc. or replicating various microstructures by electroforming to generate a negative or positive replica intermediate or final embossing tool mold. Also, microstructured molds having random and irregular shapes and patterns can be generated by chemical etching, sandblasting, shot peening or sinking discrete structured particles in a moldable material. Additionally any of the microstructured molding tools can be altered or modified according to the procedure taught in U.S. Pat. No. 5,122,902, the entire disclosure of which is herein incorporated by reference.

For illustration purposes, FIG. 1 is provided to depict a portion of an example article 10. Article 10 includes a shape memory polymer such as, for example, any of the shape memory polymers described herein. Article 10 may comprise a polymeric member that includes a surface 12 having a plurality of surface features or microstructures 14 formed therein. In this example, microstructures 14 are depicted as projections extending outward from surface 12. However, this arrangement is not intended to be limiting as a wide variety of differing arrangements are contemplated including those described above.

Depending on the application, article 10 may be in the "pre-set" shape or may be in the "deformed" shape. If article 10, as shown in FIG. 1, is in the pre-set shape, surface 12 can be deformed. This may be accomplished, for example, by changing the configuration of microstructures 14. For example, microstructures 14 may be flattened. The deformed article 10 can be shifted back to the pre-set configuration (i.e., the configuration depicted in FIG. 1 for this example) upon exposure to, for example, increased temperature, solvent, or any other suitable stimuli. Alternatively, if article 10 is in the deformed shape or configuration when arranged as shown in FIG. 1, exposure to the appropriate stimuli may shift article 10 back to the pre-set shape. In this later embodiment, the pre-set shape may include a generally flat or planar arrangement for surface 12 or any other suitable shape.

Figure 2:
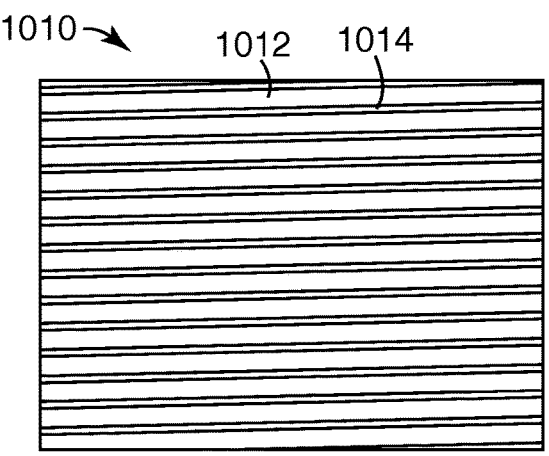
FIG. 2 is a side view of another illustrative article having a surface with a microstructure.
Figure 3:
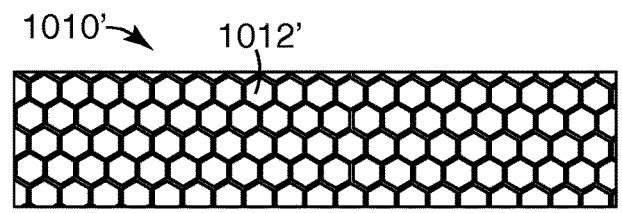
FIG. 3 is an alternative side view of the illustrative article shown in FIG. 2.

FIGS. 2-3 depict another example article 1010. Article 1010 may comprise, a sensor. In this embodiment, article 1010 may include a surface 1012 having a microstructure defined therein. The microstructure may include, for example, a plurality of rows or wells 1014. This configuration may be the pre-set shape of surface 1012. Surface 1012 can be deformed into a deformed shape that is, for example, substantially flat. A secondary surface 1012', for example on the opposite side of article 1010 (which is indicated in FIG. 3 as article 1010') may have a generally flat pre-set shape that can be deformed to have a microstructure that includes or defines a hexagonal pattern therein. Mobilizing may restore both surfaces 1012/1012'. For example, surface 1012 may shift back to the pre-set shape (see FIG. 2) and opposite surface 1012' may shift back to a substantially flat shape. In this embodiment, mobilizing may include the application of heat and/or the exposure to solvent or solvent vapors to one or both of surface 1012 and/or surface 1012'. For example, surfaces 1012/1012' may be exposed to heat and restored. Alternatively, surfaces 1012/1012' may be exposed to solvent or solvent vapors. This later embodiment may allow article 1010 to be used as a sensor that can "smell" a solvent. For example, a user may visually observe the changes in the shape of article 1010 (on one or both sides) in order to observe that the sensor has smelled a particular solvent.

FIGS. 2-3, in addition to illustrating that article 1010 can be used as a sensor, also indicate that a surface having a pre-set shape may be formed on multiple sides of an article. For example, FIGS. 2-3 illustrate article 1010 having surface 1012 with a pre-set shape that includes a microstructure whereas surface 1012' has a pre-set shape that is generally planar. In these embodiments or embodiments of the same spirit, one or both of the surfaces 1012/1012' can be deformed. For example, surface 1012 can be flattened whereas surface 1012' can be deformed to have a microstructure. Thus, article 1010 can be seen as having a secondary surface 1012' with a microstructure. It can be appreciated that secondary surface 1012' may, alternatively, have a pre-set shape that includes the microstructure shown in FIG. 3 and it can be deformed to have another shape. Moreover, the secondary surface 1012' (or other surfaces having a pre-set shape) may be defined along any area of the article 1010 and need not be limited to just a surface that is opposite of surface 1012. Regardless of the configuration of surfaces 1012/1012', mobilization shifts surfaces 1012/1012' back to their pre-set shape. It can be appreciated that other articles are contemplated that have multiple surfaces with pre-set shapes including multiple planar surfaces and/or multiple surfaces with microstructures. Moreover, other embodiments are contemplated where one or more surfaces have a microstructure formed therein and one or more of these surfaces can be deformed to have a different microstructure.

Shape Memory Polymers

As described above, the articles disclosed herein include a shape memory polymer. Shape memory polymers can be classified as elastomers. On the molecular level they represent polymer networks that include segment chains that are connected by netpoints. The netpoints can be formed by entanglements of the polymer chains or intermolecular interaction of certain polymer blocks. These cross-links are called physical netpoints. Cross-links in the form of covalent bonds form chemical netpoints. An elastomer exhibits a shape-memory functionality if the material can be stabilized in the deformed state in a temperature range that is relevant for the particular application. This can be achieved by using the network chains as a kind of molecular switch. For this purpose, it should be possible to limit the flexibility of the segments as a function of temperature. This process is supposed to be reversible. The ability to incorporate a control function into the material provides a thermal transition $T_{trans}$ of the network chains in the temperature range of interest for the particular application. At temperatures above $T_{trans}$ the chain segments are flexible, whereas the flexibility of the chains below this thermal transition is at least partially limited. In the case of a transition from the rubber-elastic, i.e., viscous, to the glassy state the flexibility of the entire segment is limited.

Without being bound to theory, it is believed that the copolymer network includes an elastomeric phase or component and a "glassy" or high glass transition temperature phase or component. The glassy phase holds or constrains the elastomeric component so that the substrate can be deformed into and stays in the deformed shape. Shifting from a deformed shape to the pre-set shape generally includes mobilizing the glassy phase of the shape memory polymer in order to allow the elastomeric component to "spring back" or otherwise shift to the original pre-set shape. According to this theory, mobilizing is understood to be the mobilization of the glassy phase through the application of the appropriate external stimuli.

In at least some embodiments, the elastomeric phase comprises a free radically polymerizable siloxane having greater than one functional free radically polymerizable group. The glassy phase may comprise at least one (meth) acrylate monomer that, when homopolymerized, forms a homopolymer having a glass transition temperature, a melting temperature, or both greater than about 40° C. According to these embodiments, exposure of the shape memory polymer to temperatures greater than 40° C. can mobilize the glassy phase and cause the deformed surface of the substrate from the deformed shape to the pre-set shape. In other embodiments, a solvent such as alkyl alcohol, acetone, etc. can partially dissolve or plasticize the glassy phase and effectuate the same change. In some embodiments, the (meth)acrylate monomer may crystallize when reacted with the free radically polymerizable siloxane having greater than one functional free radically polymerizable group. In these embodiments, exposing the copolymer network to temperatures above the melting point of the (meth)acrylate monomer may mobilize the glassy phase.

The relative proportions of the various components of the copolymer network can vary. For example, in at least some embodiments, the copolymer network may include about 10-70 weight-percent of the free radically polymerizable siloxane. In other embodiments, the copolymer network may include about 10-60 weight-percent of the free radically polymerizable siloxane. In still other embodiments, the copolymer network may include about 20-60 weight-percent of the free radically polymerizable siloxane.

Free Radically Polymerizable Siloxanes

The free radically polymerizable siloxanes for use in the copolymer networks may be represented by the following formula:

wherein:
X is a group having ethylenic unsaturation;
Y is a divalent linking group;
m is an integer of 0 to 1;
D is selected from the group consisting of hydrogen, an alkyl group of 1 to about 10 carbon atoms, aryl, and substituted aryl;
R is a divalent hydrocarbon group;
$R_1$ are monovalent moieties which can be the same or different selected from the group consisting of alkyl, substituted alkyl, aryl, and substituted aryl;
$R_2$ are monovalent moieties which can be the same or different selected from the group consisting of alkyl, substituted alkyl, aryl, and substituted aryl;
$R_3$ are monovalent moieties which can be the same or different selected from the group consisting of alkyl, substituted alkyl, vinyl, aryl, and substituted aryl;
$R_4$ are monovalent moieties which can be the same or different selected from the group consisting of alkyl, substituted alkyl, vinyl, aryl, and substituted aryl; and
n is an integer of about 10 to about 2000.

Some examples of suitable free radically polymerizable siloxanes for use in the articles described herein may include those described in U.S. Pat. No. 5,091,483, the entire disclosure of which is herein incorporated by reference.

In at least some embodiments, the free radically polymerizable siloxanes comprise telechelic siloxanes. The telechelic siloxanes may include, for example, (meth)acryloxyurea siloxane (MAUS), acrylamidoamido siloxane (ACMAS), methacrylamidoamido siloxane (MACMAS), and methylstyrylurea siloxane (MeStUS). In general, these telechelic siloxanes are formed by reacting silicone diamines with capping reagents such as isocyanatoethylmethacrylate (IEM), vinyldimethylazlactone (VDM), isopropenyl dimethyl azlactone (IDM), and m-isopropenyl alpha, alpha-dimethyl benzyl isocyanate (m-TMI), respectively. These telechelic siloxanes may have a number average molecular weights in the range of about 1,000 to 200,000. Some additional details regarding synthesis is provided below. Particularly preferred telechelic siloxanes are those that include a polydimethylsiloxane chain and may also be referred to as polydimethylsiloxanes.

The telechelic siloxanes have free radically polymerizable end groups. Due to the polar nature of the hydrogen bonding end groups and the nonpolar nature of the polydimethylsiloxane chain, a transient network is formed wherein the polar end groups tend to associate with each other. The relative strength of the end group association for the various telechelic siloxanes is reflected in their viscosities, with higher viscosities seen in the case of the more strongly associating end groups (e.g., ACMAS and MeStUS).

Functional polymers, like these telechelic siloxanes, that are easy to cure to elastomers are often referred to as "liquid rubbers." Indeed, by the exposure of telechelic siloxanes having free radically polymerizable end groups to low-intensity UV radiation (when the system contains photoinitiator), silicone elastomers with controlled properties can be obtained.

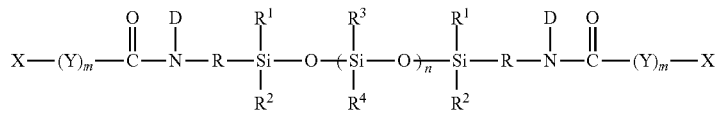

In general the telechelic siloxanes are obtained from amine-functional siloxane intermediates. Suitable polydiorganosiloxane diamines and methods of making the polydiorganosiloxane diamines are described, for example, in U.S. Pat. Nos. 3,890,269 (Martin), 4,661,577 (Jo Lane et al.), 5,026,890 (Webb et al.), 5,276,122 (Aoki et al.), 5,214,119 (Leir et al.), 5,461,134 (Leir et al.), 5,512,650 (Leir et al.), and 6,355,759 (Sherman et al.), incorporated herein by reference in their entirety. Some polydiorganosiloxane diamines are commercially available, for example, from Shin Etsu Silicones of America, Inc., Torrance, Calif. and from Gelest Inc., Morrisville, Pa. Particularly useful polydiorganosiloxane diamines include bis(3-aminopropyl)polydimethylsiloxanes.

Polydimethylsiloxanes having acrylamidoamido end groups (ACMAS) can be prepared by the reaction of a polydimethylsiloxane diamine with 2 equivalents of vinyl dimethyl azlactone (VDM). Similarly, polydimethylsiloxanes having methacrylamidoamido end groups (MACMAS) can be prepared in the same manner by the reaction of a polydimethylsiloxane diamine with 2 equivalents of isopropenyl dimethyl azlactone (IDM).

Polydimethylsiloxanes having methacryloxyurea end groups (MAUS) can be prepared using the same procedure, by the reaction of a polydimethylsiloxane with 2 equivalents of isocyanatoethyl methacrylate (IEM).

Polydimethylsiloxanes having alpha-methylstyrylurea end groups (MeStUS) can be made by the reaction of a polydimethylsiloxane with 2 equivalents of m-isopropenyl-alpha,alpha-dimethyl benzyl isocyanate (m-TMI).

In other embodiments the free radically polymerizable siloxanes comprise non-techelic siloxanes. These siloxanes are ones according to the above formula where at least some of the groups $R_3$ and/or $R_4$ comprise vinyl groups.

(Meth)acrylate Monomers

Generally, (meth)acrylate monomers are monomers that are the (meth)acrylate esters of non-tertiary alkyl alcohols, the alkyl groups of which comprise from about 1 to about 20, or about 1 to about 18 carbon atoms. Suitable (meth)acrylate monomers include, for example, benzyl methacrylate, cyclohexyl acrylate, cyclohexyl methacrylate, ethyl methacrylate, isobornyl acrylate, isobornyl methacrylate, methyl methacrylate, 1-methylcyclohexyl methacrylate, 2-methylcyclohexyl methacrylate, 3-methylcyclohexyl methacrylate, 4-methylcyclohexyl methacrylate, and 2-phenoxy ethyl methacrylate.

Particularly suitable (meth)acrylate monomers are those that, when homopolymerized, form a homopolymer having a glass transition temperature, a melting temperature, or both greater than about 40° C. These monomers are suitable in forming a copolymer network with a free radically polymerizable siloxane. Examples of preferred (meth)acrylate monomers include isobornyl acrylate, cyclohexyl acrylate, trimethyl cyclohexyl acrylate, methyl methacrylate, methacrylic acid, t-butyl acrylate. A single (meth)acrylate monomer or a combination of (meth)acrylate monomers may be used.

The glass transition temperature (and/or the melting temperature) may be measured by conventional techniques such as Differential Scanning Calorimetry (DSC) or Dynamic Mechanical Analysis (DMA). Some additional details regarding these components of the copolymer network are described in more detail below.

Curing Initiator

As indicated above, the shape memory polymer may be a copolymer network including the reaction product of a free radically polymerizable siloxane having greater than one functional free radically polymerizable group and at least one (meth)acrylate monomer. The reaction may include, for example, polymerization via curing. Curing may be carried out in an oxygen-free, e.g., in an inert atmosphere such as nitrogen gas or by utilizing a barrier of radiation-transparent material having low oxygen permeability. Curing can also be carried out under an inerting fluid such as water. When visible or ultraviolet radiation is used for curing, the reaction may also contain a photoinitiator. Suitable photoinitiators include benzoin ethers, benzophenone and derivatives thereof, acetophenone derivatives, camphorquinone, and the like. Some examples of commercially available photoinitiaors include DARACUR 1173, DAROCUR 4265, IRGACURE 651, IRGACURE 1800, IRGACURE 369, IRGACURE 1700, and IRGACURE 907, commercially from Ciba Geigy. The photoinitiator may be used at a concentration of from about 0.1% to about 5% by weight of the total polymerizable composition, and, if curing is carried out under an inerting fluid, the fluid is preferably saturated with the photoinitiator or photoinitiators being utilized in order to avoid the leaching of initiator from the reaction. The rapid cure observed for these materials allows for the use of relatively low levels of photoinitiator, hence uniform cure of thick sections can be achieved due to deeper penetration of radiation. If desired, curing can also be achieved thermally, which may include the use of thermal initiator such as peroxides, azo compounds, or persulfates generally at a concentration of from about 1% to about 5% by weight of the total polymerizable composition. In at least some embodiments, any initiator (thermal or photo-) utilized may be soluble in the reaction components themselves, thereby avoiding the need for a separate solvent. Liquid initiators may be preferred.

Preparation of Silicone-Acrylate Copolymeric Networks

Polymerization mixtures can be prepared by dissolving telechelic siloxanes in the (meth)acrylate monomers and adding a photoinitiator Such polymerization mixtures typically have viscosities that permit the preparation of samples in film form by direct coating and radiation curing by standard procedures.

The shape memory polymer article may be formed by coating and curing the polymerizable mixture in a structured configuration, by curing the polymerization mixture in an unstructured configuration and then applying a structure through the imposition of heat and pressure, or by a combination of the these processes.

For example, the polymerization mixture can be coated onto a carrier layer such as a liner (either structured or unstructured), onto a substrate (such as a metal sheet or foil, a film, a ceramic or piece of glass, etc) or onto a tool or mold. The coated polymerization mixture is then covered with a covering layer which may be another liner, substrate, tool or mold and may be the same or different from the carrier layer. The resulting construction is then cured, preferably with UV radiation. Upon curing one or both of the carrier layer and or the covering layer are removed and the shape memory polymer article may then be subjected to additional processing (to create or remove structuring, to form in articles of a desired shape, etc).

The entire disclosures of the following patents, which are referred to in the various Examples, are herein incorporated by reference: U.S. Pat. Nos. 5,514,730 5,706,132, and 6,569,521.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

| Table of Abbreviations | |
|---|---|
| Abbreviation or Trade Designation | Description |
| 5K MAUS | Methacryloxyurea siloxane, a difunctional silicone acrylate prepared from PDMS diamine 5K as described in U.S. Pat. No. 5,514,730 column 14 for 35K MAUS, using 5,000 g/mole PDMS diamine instead of 35,000 g/mole PDMS diamine. |
| PDMS | Polydimethyl siloxane |
| DAROCUR 1173 | Photoinitiator: 2-hydroxy-2-methyl-1-phenyl-propan-1-one from Ciba Specialty Chemicals, Hawthorne, NY. |
| PET | Unprimed polyester film of polyethylene terephthalate having a thickness of 50 or 125 micrometers. |
| 5K MeStUS | Alpha-methyl styrylurea siloxane, a difunctional silicone alpha-methyl styrene prepared from PDMS diamine 5K as described in U.S. Pat. No. 5,514,730 column 14 for 35K MeStUS, using 5,000 g/mole PDMS diamine instead of 35,000 g/mole PDMS diamine. |
| 5K ACMAS | Acrylamidoamido siloxane, a difunctional silicone acrylamido prepared from PDMS diamine 5K as described in U.S. Pat. No. 5,514,730 column 14 for 35K ACMAS, using 5,000 g/mole PDMS diamine instead of 35,000 g/mole PDMS diamine. |
| 50K MAUS | Methacryloxyurea siloxane, a difunctional silicone acrylate prepared from PDMS diamine 50K as described in U.S. Pat. No. 5,514,730 column 14 for 35K MAUS, using 50,000 g/mole PDMS diamine instead of 35,000 g/mole PDMS diamine. |
| 50K MeStUS | Alpha-methyl styrylurea siloxane, a difunctional silicone alpha-methyl styrene prepared from PDMS diamine 50K as described in U.S. Pat. No. 5,514,730 column 14 for 35K MeStUS, using 50,000 g/mole PDMS diamine instead of 35,000 g/mole PDMS diamine. |
| 50K ACMAS | Acrylamidoamido siloxane, a difunctional silicone acrylamido prepared from PDMS diamine 50K as described in U.S. Pat. No. 5,514,730 column 14 for 35K ACMAS, using 50,000 g/mole PDMS diamine instead of 35,000 g/mole PDMS diamine. |
| Water-borne PSA | Acrylate polymer dispersion at 40% solids. |

Example 1

A curable precursor solution of 40 parts of 5K MAUS dissolved in 60 parts of IBA, containing 0.5 wt % DAROCUR 1173 was poured on the first tool, which was an unstructured PET film laid down on the surface of a glass plate. The first tool was bordered by a compliant adhesive film of 3 millimeters thickness to serve as a dam for the curable adhesive precursor as well as a spacer to control the thickness of the cured film. The liquid layer of curable precursor was covered with a cover sheet (an unstructured UV transparent film) and the excess fluid was squeezed out by placing a rigid glass plate over the cover sheet and pressing the thus formed sandwich construction until the glass plate rested against the spacer. The sandwich construction was exposed to low intensity UV lights through the cover sheet for 10-15 minutes. The resulting cured film (slab) had two surfaces replicated from the first tool and from the cover sheet (second tool) and was removed from both the first tool and from the cover sheet. The edges of the substrate were trimmed.

Example 2

The slab prepared in Example 1 was deformed by pressing against the structured surface of the metal tool and a polished steel plate with heat/pressure (110° C. for 10 minutes, pre-press 4.1 MegaPascals (600 lbs/in$^2$) for 10 minutes, 30 MegaPascals (2 ton/in$^2$) high pressure for 10 minutes) and quenched (25 minutes until temperature reached 60° C.). The structure of the tool—an array of tilted triangular prisms with millimeter-size dimensions, was partially replicated—approximately 60-70% of the height of the pyramid.

Example 3

A part of the film made in Example 2 was heated to approximately 110° C. on a heating plate. The area exposed to heat became essentially flat, with some traces of the embossed microstructure still visible.

Example 4

A shape-memory substrate was prepared as described in Example 2. One part of the sample was submitted to a secondary process of shaving off the temporary surface features. When the sample was heated to 120° C. the portion of the sample with shaved-off material showed rounded cavities with topologies corresponding to the shaved-off elements.

Example 5

A shape-memory substrate was prepared as described in Example 1 except that the first tool was a microstructured film having linear array of rectangular channels (200 micrometers at the bottom, 100 micrometers at the top, 200 micrometer high) and a 1 millimeter spacer was used. The sample was flattened between the two polished steel plates under the conditions as described in Example 2 except flat tools were used. One part of the film was sprayed with metallic silver paint to form a thin layer of metallic silver. The electrical conductivity of the sample was checked using a Fluke 87 III RMS Multimeter, which was independent of the position of the electrodes (x and y conductive). A portion of the sample was heated to 120° C. on a heating plate to restore the original shape of the surface. Electrical conductivity of the sample was again checked. While the sample maintained the electrical conductivity along the channels the conductivity in the cross-direction was primarily destroyed and/or disrupted.

Example 6

A shape-memory substrate was made as described in Example 1 except that the first tool was a metal tool with structured surfaces as described in Example 2. The substrate having sharp macroscopic features was subsequently submitted to heat and pressure between two polished steel plates under the conditions described in Example 2 except flat tools were used. The substrate became essentially flat with the pyramids being partially flattened and partially bent. Part of the original structure was restored by selectively focusing sunlight through a lens onto several of the pyramids.

Example 7

A shape-memory substrate was tested through the stages of making, distorting and restoring. The sample was made as described in Example 1 except that the first tool was a metal tool having an array of cube corners as described in U.S. Pat. No. 5,706,132. The pyramids had a height of 87 micrometers (3.5 mil). The spacer used was 125 micrometers. The sample was removed from the first tool while maintained on the flat PET cover. The sample showed retroreflectivity when analyzed using a retroviewer (the sample "made" stage). A part of the sample was flattened between the two polished steel plates under the conditions described in Example 2 except that the tools were flat. It was noticed that the height of the pyramids were reduced, but the pyramidal shape of the flattened microfeatures was maintained (the sample "distorted" stage). The sample showed no retroreflectivity in a retroviewer. A portion of the sample was heated to 120° C., which restored the original shape of the pyramids and the retroreflectivity of the sample (the sample "restored" stage).

Example 8-13

A series of samples were made, distorted and restored as in Example 7 except that different compositions of the curable precursors were used (containing Monomer 1, IBA and DAROCUR 1173) as shown in Table 1. Results of the testing are shown in Table 2.

TABLE 1

| Example | Monomer 1 Identity | Monomer 1 (parts) | IBA (parts) | DAROCUR 1173 (wt %) |
|---|---|---|---|---|
| 8 | 5K MeStUS | 50 | 50 | 0.5 |
| 9 | 5K MAUS | 50 | 50 | 0.5 |
| 10 | 5K ACMAS | 50 | 50 | 0.5 |
| 11 | 50K MeStUS | 50 | 50 | 0.5 |
| 12 | 50K MAUS | 50 | 50 | 0.5 |
| 13 | 50K ACMAS | 50 | 50 | 0.5 |

TABLE 2

| Example | Sample Color | Appearance As Made | Distortion | Appearance After Distortion | Appearance As Restored |
|---|---|---|---|---|---|
| 8 | Clear | Retroreflective Cubes | Flattened to 0.6 micrometers | No retroreflection | Retroreflective Cubes |
| 9 | Clear | Retroreflective Cubes | Flattened to 1.0 micrometers | No retroreflection | Retroreflective Cubes |
| 10 | Bluish Haze | Retroreflective Cubes | Flattened to 2.0 micrometers | No retroreflection | Retroreflective Cubes |
| 11 | Clear | Retroreflective Cubes | Flattened to 1.0 micrometers | No retroreflection | Retroreflective Cubes |
| 12 | Clear | Retroreflective Cubes | Flattened to 1.5 micrometers | No retroreflection | Retroreflective Cubes |
| 13 | Clear | Retroreflective Cubes | Flattened to 7.8 micrometers | No retroreflection | Retroreflective Cubes |

Example 14

A shape-memory substrate was made as described in Example 1 except that a 125 micrometers spacer was used. One of the surfaces of the substrate was deformed by pressing the sample between the metal tool, having regularly arranged square posts (150 micrometers at the bottom, 150 micrometers at the top, 50 micrometers high), to create a corresponding array of microcavities. The substrate was coated with a Water-borne PSA. Upon drying the water at 25° C. for 24 hours, the film contained PSA distributed within the pockets of microstructure substrate and showed no/little tack. A portion of the sample was heated to 120° C. on a heating plate causing the restoration of the original flatness of the substrate and making the sample tacky by exposing the PSA layer on the surface.

Example 15

A shape-memory substrate was made as described in Example 1 except that a 1 millimeter spacer was used. One of the surfaces of the substrate was deformed by pressing the sample between the metal tool, having an array of triangular posts (420 micrometers depth), to create an array of visible cavities. The substrate was flooded with colored aqueous fluid to fill the cavities. Silicone pressure sensitive adhesive tape (as described in U.S. Pat. No. 6,569,521, Example 28) was laminated to the substrate to seal off the cavities filled with the fluid. When heated to 120° C. the substrate returned to its original shape exerting pressure on the laminated tape causing the tape to also distort, and causing the adhesive border seals to rupture.

Example 16

A shape-memory substrate was made as described in Example 1, except that the first tool was a metal tool, a replica of the tool used to deform the substrate in Example 14, having regularly arranged square cavities (150 micron at the bottom, 150 micron at the top, 45 micrometer high) and a 1 millimeter spacer to create a corresponding array of micro-posts. The sample was flattened between two polished steel plates under the conditions as described in Example 2. The sample was heated to 120° C. on a heating plate to restore the original structure (posts) of the surface. The posts were able to pick up water-based ink for transfer to paper.

Example 17

A shape-memory substrate was made as described in Example 1 except that a 125 micrometers spacer was used. One of the surfaces of the substrate was deformed by pressing the sample between the metal tool having regularly arranged square posts, as described in Example 14, to create a corresponding array of micro-cavities. When a droplet of the solution of dye (bromothymol blue, sodium salt) in ethylene glycol was deposited on the surface of the film, clear-cut borders along the line of the pattern were naturally established, and the solvent essentially restored the "printed" area to flatness with the clearly visible high concentration of the dye in the spots corresponding to the arrangement of cavities in which it was originally deposited.

Example 18

A shape-memory substrate was made as described in Example 1 except that a 125 micrometers spacer was used and the first tool was a metal tool with an array of square posts, as described in Example 14. The cured sample was pressed between 2 flat surfaces using the technique described in Example 2. When a droplet of the solution of dye (bromothymol blue, sodium salt) in ethylene glycol was deposited on the surface of the film, clear-cut borders along the line of the pattern were naturally established, and the solvent essentially restored the "printed" area to its microcavitated form dragging the ink into the cavities.

Examples 19

A shape-memory substrate was made as described in Example 1 except that a 125 micrometers spacer was used. One of the surfaces of the cured substrate was deformed by pressing the sample between the metal tool, used in Example 16. A droplet of the aqueous solution of dye (bromophenol blue indicator solution) was deposited and pressed on the microstructured surface of the shape-memory substrate. The solution was primarily distributed in the channels between the posts, and on the top of the posts having some small micro-channels. When exposed to heat (120° C.), the solvent (water) evaporated and the flatness of the first surface of the substrate was essentially restored leaving a regular pattern of the dye on the surface.

Example 20

A shape-memory substrate was made as described in Example 1 except that a 125 micrometers spacer was used. One of the surfaces of the substrate was deformed by pressing the sample between the metal tool (an array of cube corners as described in U.S. Pat. No. 5,706,132, pyramidal height of 87 micrometers), as described in Example 2. A border of adhesive was made on a plastic substrate and the microstructured surface was placed within and on the border. The retroreflectivity of the microstructured surface disappeared where in contact with the adhesive border, but remained retroreflective within the border.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. An article consisting of:
a first portion consisting of:
a polymeric member including a surface having a microstructure, wherein the microstructure is formed through the use of a microstructured molding tool; and
wherein the polymeric member consists of a shape memory polymer, the shape memory polymer consisting of a copolymer network consisting of the reaction product of a free radically polymerizable siloxane having greater than one functional free radically polymerizable group, at least one (meth)acrylate monomer, and a photoinitiator, wherein the at least one (meth)acrylate monomer, when homopolymerized, forms a homopolymer having a glass transition temperature, a melting temperature, or both greater than about 40° C.; and
a second portion consisting of a metal, a metal alloy, a ceramic, or a fluid.

2. The article of claim 1, wherein the free radically polymerizable siloxane has a number average molecular weight of about 1,000-200,000 grams per mole.

3. The article of claim 1, wherein the free radically polymerizable siloxane includes a telechelic siloxane.

4. The article of claim 2, wherein the telechelic siloxane includes (meth)acryloxyurea siloxane.

5. The article of claim 2, wherein the telechelic siloxane includes acrylamidoamido siloxane.

6. The article of claim 2, wherein the telechelic siloxane includes methacrylamidoamido siloxane.

7. The article of claim 2, wherein the telechelic siloxane includes methylstyrylurea siloxane.

8. The article of claim 1, wherein the (meth)acrylate monomer includes isobornyl acrylate.

9. The article of claim 1, wherein the copolymer network includes about 10-70 weight-percent of the free radically polymerizable siloxane.

10. The article of claim 1, wherein the copolymer network includes about 10-60 weight-percent of the free radically polymerizable siloxane.

11. The article of claim 1, wherein the copolymer network includes about 20-60 weight-percent of the free radically polymerizable siloxane.

12. The article of claim 1, wherein the polymeric member includes a secondary surface having a microstructure.

13. An article, consisting of:
a polymeric member including a microstructured surface, wherein the microstructured surface includes a surface feature that is not visible to an unaided eye, and wherein the microstructure is formed through the use of a microstructured molding tool; and
wherein the polymeric member consists of a shape memory polymer, wherein the shape memory polymer consists of a copolymer network consisting of the reaction product of a free radically polymerizable siloxane having greater than one functional free radically polymerizable group, at least one (meth)acrylate monomer, and a photoinitiator; and
a metal, a metal alloy, a ceramic, or a fluid.

14. The article of claim 13, wherein the shape memory polymer consists of a copolymer network consisting of the reaction product of a free radically polymerizable siloxane having greater than one functional free radically polymerizable group and at least one (meth)acrylate monomer, wherein the at least one (meth)acrylate monomer, when homopolymerized, forms a homopolymer having a glass transition temperature, a melting temperature, or both greater than about 40° C.

15. The article of claim 14, wherein the free radically polymerizable siloxane has a number average molecular weight of about 1,000-200,000 grams per mole.

16. The article of claim 14, wherein the (meth)acrylate monomer includes isobornyl acrylate.

17. The article of claim 14, wherein the free radically polymerizable siloxane includes a telechelic siloxane.

18. The article of claim 17, wherein the telechelic siloxane includes (meth)acryloxyurea siloxane, acrylamidoamido siloxane, methacrylamidoamido siloxane, or methylstyrylurea siloxane.

19. The article of claim 13, wherein the surface feature includes a plurality of depressions.

20. The article of claim 13, wherein the surface feature includes a plurality of projections.

21. The article of claim 13, wherein the polymeric member includes a secondary surface having a microstructure.

22. An article, consisting of:
  a polymeric member including a microstructured surface, wherein the microstructured surface includes a surface feature that is not visible to an unaided eye, and wherein the microstructure is formed through the use of a microstructured molding tool; and
  wherein the polymeric member consists of a shape memory polymer, the shape memory polymer consisting of a copolymer network consisting of the reaction product of (meth)acryloxyurea siloxane, isobornyl acrylate, and a photoinitiator; and
  a metal, a metal alloy, a ceramic, or a fluid.

\* \* \* \* \*